United States Patent [19]

Li

[11] 4,302,617
[45] Nov. 24, 1981

[54] CONVERSION OF ETHYL CHLORIDE TO VINYL CHLORIDE

[75] Inventor: Tao P. Li, Chesterfield, Mo.

[73] Assignee: Monsanto Co., St. Louis, Mo.

[21] Appl. No.: 856,840

[22] Filed: Dec. 2, 1977

[51] Int. Cl.³ .............................................. C07C 17/24
[52] U.S. Cl. .................................................... 570/230
[58] Field of Search ....................... 260/656 R, 654 D; 570/230

[56] References Cited

U.S. PATENT DOCUMENTS

| | | | |
|---|---|---|---|
| 2,342,100 | 2/1944 | Cass | 260/656 R |
| 3,207,806 | 9/1965 | Bajars | 260/654 D |
| 3,267,161 | 8/1966 | Ukaji et al. | 260/656 R |
| 3,308,197 | 3/1967 | Bajars | 260/656 R |
| 3,356,750 | 12/1967 | Bojanowski et al. | 260/656 R |
| 3,462,502 | 8/1969 | Hornig et al. | 260/654 A |
| 3,513,207 | 5/1970 | Hornig et al. | 260/654 A |
| 3,872,027 | 3/1975 | Christmann et al. | 260/656 R |

FOREIGN PATENT DOCUMENTS 1597813  6/1970  France ........................... 260/654 A

*Primary Examiner*—Delbert E. Gantz
*Assistant Examiner*—Joseph A. Boska

[57] ABSTRACT

Monohalogenated olefins are prepared from halo-alkanes containing 2 to 6 carbon atoms and at least two hydrogen atoms on adjacent carbons by dehydrogenation of the halo-alkanes at a temperature from about 400° to about 700° C. in the presence of oxygen and in contact with a catalyst comprising a halide of copper and an alkali metal phosphate, particularly potassium phosphate, deposited upon an inorganic support. Typically, vinyl chloride is prepared from ethyl chloride.

11 Claims, No Drawings

CONVERSION OF ETHYL CHLORIDE TO VINYL CHLORIDE

BACKGROUND OF THE INVENTION

The present invention relates to the production of monohalogenated olefins directly from halogen-containing alkanes. More particularly, it relates to the production of vinyl chloride by oxydehydrogenation of ethyl chloride in contact with a catalyst which provides high yields of the vinyl chloride product.

In many processes for producing vinyl chloride, a co-product of the reaction is ethyl chloride. The ethyl chloride may be separately recovered as such or may be recycled in some processes for further chlorination to dichloroethane and ultimate conversion to vinyl chloride by dehydrohalogenation either thermally or catalytically. Another route for conversion of the by-product ethyl chloride to produce additional vinyl chloride involves dehydrohalogenation to ethylene followed by oxychlorination of this hydrocarbon directly to the desired vinyl chloride or conversion of ethylene to produce 1,2-dichloroethane which on pyrolysis yields vinyl chloride. Not much attention has been given to direct production of vinyl chloride from ethyl chloride by dehydrogenation of the ethyl chloride although in U.S. Pat. No. 3,356,750 such a process is described. According to this patent, a haloalkane having 2 to 4 carbon atoms such as ethyl chloride is dehydrogenated by passing it in admixture with oxygen and molecular iodine at a temperature in the range from 400° C. to 800° C. and at a partial pressure of halogen-containing alkane equivalent to less than about 15 inches of mercury through a reactor containing metals or active compounds thereof of Groups I-A, II-A, II-B, III-A, III-B, IV-A, IV-B, V-A, V-B, VI-B, VII-B, VIII and the lanthanum rare earth group of the Periodic Table. While a high yield of vinyl chloride is said to be obtained with this method, the problems of handling the highly volatile and corrosive iodine reactant are formidable when practicing this process on a commercial scale. Accordingly, it is an object of the present invention to provide a process for dehydrogenation of ethyl chloride to vinyl chloride which operates at somewhat lower temperatures, eliminates iodine as a reactant and yet provides comparable high yields of vinyl chloride in view of the excellent selectivity of a novel catalyst which has been discovered. In addition to providing a means for converting to vinyl chloride the ethyl chloride obtained as a by-product in chlorination reactions, the process of the invention provides a means for producing vinyl chloride from ethane as the hydrocarbon source instead of ethylene.

STATEMENT OF THE INVENTION

According to the invention, a monohalogenated olefin is prepared by a process wherein a halo-alkane containing 2 to 6 carbon atoms and at least two hydrogen atoms on adjacent carbon atoms is dehydrogenated at a temperature in the range from about 400° to 700° C. in the presence of oxygen and in contact with a catalyst comprising a halide of copper and an alkali metal phosphate supported on an inorganic material. In its more specific form, the invention relates to the production of vinyl chloride by the oxidative dehydrogenation of ethyl chloride at a temperature in the range from about 500° to about 600° C. in contact with a catalyst comprising copper chloride and potassium phosphate.

DESCRIPTION OF THE PREFERRED EMBODIMENTS

The catalyst employed in the process of the invention is readily prepared by admixing of the support material or carrier with a solution of the copper halide or of the copper halide and any other metal halides which are to be included in the catalyst composition in the proper amount in water or, preferably, in an alcohol. After thorough mixing, the solids are separated from the mixture or slurry either mechanically and/or by evaporation of the solvent and then subjected to drying at a temperature from about 100° to about 200° C. for a period of from about one to about ten hours. The solid remaining is converted into any desired form by grinding, pelletizing, etc., after which it is heat-treated while under fluidization conditions with air at a temperature from about 300° to about 600° C. for a period from about 2 to about 8 hours and preferably at a temperature of about 450° C. for about 3 to about 6 hours.

Various materials may serve as suitable supports for the catalyst of the present invention. Among the many which can be used may be mentioned alumina, silica gel, silica-alumina, silicamagnesia, bauxite, magnesia, silicon carbide, titania, zirconium silicate and the like. The preferred support is alumina. The surface area of the support may range up to 150 $m^2/g$. Catalyst supports having a low surface area, i.e., <30 $m^2/g$ are preferred while those of <10 $m^2/g$ are especially preferred. Available support materials of high surface area may be readily calcined to reduce their surface area to the desired level.

The concentration of copper on the support may vary from about 0.1 to about 10% by weight and preferably is from about 1 to about 5% by weight. The concentration of alkali metal as the phosphate is from about 1% by wt. to about 10% by wt. and preferably is from about 3 to about 6% by weight. Compounds of so-called platinumgroup metals can also be incorporated in the catalyst composition. Compounds of such metals as platinum, palladium, rhodium, ruthenium, osmium, and iridium, particularly the halide of these metals, may have a beneficial effect on the reaction. When a platinum-group metal is employed with the copper, the concentration of this metal is generally in the range from about 0.1% by weight to about 1% by weight and preferably is about 0.5% by weight. Alkali metal halides may also be incorporated if desired in the catalyst composition. The amounts of the latter if they are used will generally vary between about 0.5 to about 5.0% by weight.

The process of the invention is particularly applicable in the manufacture of monochlorinated and monobrominated olefins from the corresponding alkyl halides which contain at least one hydrogen atom on adjacent carbon atoms and 2 to 6 carbon atoms. It has particular utility in providing vinyl chloride in good yield from ethyl chloride but is also useful, for example, for producing allyl chloride from propyl chloride, vinyl bromide from ethyl bromide, vinyl dichloride from ethyl dichloride, 3-chlorobutene-1 from butyl chloride, 2-chlorobutene from 2-chlorobutane as well as butadiene from both, and the like.

Elemental oxygen is supplied to the reaction either pure or diluted with inert gases such as nitrogen, helium, carbon dioxide and the like or as air. Excess haloalkane may be employed if desired but is not necessary.

The relative molar proportions of haloalkane and oxygen are generally in the range from about 1:0.25 to about 1:2 and preferably from about 1:0.5 to about 1:1 in the preferred temperature range.

The reaction can be conducted at temperatures from about 400° to about 700° C. but preferably reaction temperatures are maintained in the temperature range from 500° to 600° C. Suitable pressures are those in the range from atmospheric to about 100 psig. Preferably, pressure is maintained at approximately atmospheric.

The process may be conducted using either a fixed bed, a moving bed, or a fluidized bed of catalyst but the fluidized bed technique is preferred. The reactants may be charged to the bottom of the reactor containing the catalyst in a finely divided state thus serving to fluidize the catalyst. The minimum gas velocity for fluidizing the catalyst is low. Linear gas velocities of the order of 0.1 to 0.5 foot per second are generally satisfactory and avoid excessive carryover of catalyst fines. The depth of the catalyst bed should be such as to permit a satisfactory fluidized condition of the catalyst to be achieved and to provide sufficient contact time for substantial conversion to the desired product at the temperature employed.

The residence or contact time of the reactants in the reaction zone under any given set of reaction conditions depends upon all of the factors involved in the reaction. Contact times ranging from about 0.1 to about 5 to 10 or 15 seconds are satisfactory. Preferably, contact times are maintained in the range from about 1 to about 5 seconds. Conversions and yields given in the tables are defined as follows:

$$\% \text{ EtCl}^1 \text{ Conversion} = \frac{\text{EtCl reacted}}{\text{EtCl in feed}} \times 100$$

$$\% \text{ VCM}^2 \text{ Yield} = \frac{\text{VCM produced}}{\text{EtCl reacted}} \times 100$$

[1]EtCl = Ethyl chloride
[2]VCM = Vinyl chloride

EXAMPLE 1

A catalyst containing 3.0% copper, 0.5% lithium, 0.5% platinum and 3% potassium as potassium phosphate having a surface area of 7.4 m²/g was prepared as follows. To a solution of 0.5494 g of the hexahydrate of hydrochloroplatinic acid ($H_2PtCl_6 \cdot 6 H_2O$), 1.2241 g of lithium chloride (LICl) and 2.5614 g of copper chloride ($CuCl_2$) in 50 ml of methanol there was added with thorough mixing 40 g of alumina known by the trade name "Alcoa F-1" which had been calcined at 1100° C. to provide a surface area of 9.4 m²/g. The resulting mixture was subjected to evaporation and dried at 100° C. for about 2 hours. It was then transferred to a fluidized bed reactor and fluidized with nitrogen at 400° C. for 6 hours. After the heat-treatment, the solid material was added to a solution of 2.1683 g of $K_3PO_4$ in 30 ml of $H_2O$ and mixed thoroughly. The liquid was evaporated from the mixture after which it was fluidized with air at 400° C. for three hours.

A series of runs were made in which ethyl chloride was dehydrogenated in the presence of oxygen using the above-described catalyst. About 20 ml (22 g) of the catalyst was charged to a pyrex reactor, one inch in diameter and 24 inches long, equipped with rotameters for measuring gas flow, flow regulations and pressure controllers. The reactor was equipped with Nichrome heating tape and asbestos insulation. Reactor temperature was measured by means of thermocouples located at five different points in the thermowell from the bottom to the top of the reactor. The catalyst was maintained in a fluidized condition by introduction of the gaseous reactants at the bottom of the reactor. Catalyst fines carried out by the reactor were accumulated in a collector heated by an electric tape to a temperature from 140° to 150° C. to prevent condensation of liquid product. The effluent gases were then passed through suitable condensers and water and liquid product were collected in suitable receivers. Off-gas was sent through a hydrogen chloride scrubber and then vented. Unreacted HCl was collected in water and titrated using a standard alkali solution. Product composition was determined by gas chromatographic analysis of an off-gas sample taken from a sampling valve located ahead of the HCl scrubber. Conditions of reaction and the results obtained in the runs are presented in Table 1.

TABLE 1

| Run No. | Temp. °C. | Contact Time, Sec. | $C_2H_5Cl$/Air (Moles) | $C_2H_5Cl$ Conv., % | VCM Yield, % |
|---|---|---|---|---|---|
| 1 | 600 | 0.44 | 1/4.76 | 79.7 | 59.2 |
| 2 | 550 | 0.47 | 1/4.76 | 65.1 | 59.3 |
| 3 | 500 | 1.0 | 1/4.76 | 67.3 | 58.4 |
| 4 | 550 | 0.95 | 1/4.76 | 86.7 | 68.2 |
| 5 | 400 | 1.15 | 1/4.76 | 14.3 | 24.1 |
| 6 | 450 | 1.07 | 1/4.76 | 30.4 | 42 |
| 7 | 600 | 0.89 | 1/4.76 | 95.9 | 70.9 |
| 8 | 500 | 2.0 | 1/4.76 | 84.3 | 67.4 |
| 9 | 500 | 0.5 | 1/4.76 | 60.5 | 52.7 |
| 10 | 500 | 1.0 | 1/7.15 | 68.3 | 55.3 |
| 11 | 500 | 1.0 | 1/9.5 | 69.2 | 47.8 |
| 12 | 500 | 1.0 | 1/2.38 | 61.8 | 69 |

EXAMPLE 2

Ethyl chloride was dehydrogenated in the presence of oxygen using a catalyst containing copper and potassium phosphate supported on alumina. The catalyst was prepared as follows.

Approximately 40.3 g of alumina supplied commercially by Aluminum Co. of America and known to the trade as "Alcoa F-1" alumina having a particle size of about 50–100 mesh was treated with hot air at 1150° C. for 64 hours to provide alumina having a surface area of 12.4 m²/g. The alumina was then impregnated with a solution of 2.56 g of $CuCl_2$ in 35 ml of methanol. The mixture was subjected to evaporation, dried and heat-treated under fluidization conditions at 450° C. with nitrogen for 3 hours and with air for 3 hours.

After heat treatment there was added to the mixture a solution of 4.4 g of $K_3PO_4$ in 35 ml of water. The resulting mixture was then dried and heat-treated under fluidization conditions at 450° C. for about three hours. The finished catalyst had a surface area of 4.0 m²/g and contained 3.0% copper and 9.0% potassium as $K_3PO_4$.

The reaction was carried out in the same apparatus and following the same procedure given in Example 1 above. Reaction conditions and results are presented in Table 2 below.

TABLE 2

| Run No. | Temp. °C. | Contact Time, Sec. | $C_2H_5Cl$/Air (Moles) | $C_2H_5Cl$ Conv., % | VCM Yield, % |
|---|---|---|---|---|---|
| 1 | 500 | 1.73 | 1/4.76 | 79 | 49.9 |
| 2 | 550 | 1.64 | 1/4.76 | 91.1 | 63.6 |

What is claimed is:
1. A process for producing monohalogenated olefins which comprises dehydrogenating in the presence of oxygen a haloalkane containing 2 to 6 carbon atoms and at least two hydrogen atoms on adjacent carbon atoms at a temperature in the range from about 400° to about 700° C. in contact with a catalyst comprising a halide of copper and an alkali metal phosphate on an inorganic support.

2. The process of claim 1 wherein said support is alumina.

3. The process of claim 2 wherein said haloalkane is ethyl chloride.

4. The process of claim 3 wherein said copper halide is cupric chloride and said alkali metal phosphate is potassium phosphate.

5. The process of claim 4 wherein the concentration of copper in said catalyst is from about 0.1 to about 10% by weight and the concentration of potassium as the phosphate is from about 1% to about 10% by weight.

6. The process of claim 5 wherein said catalyst has a surface area of $<10$ m$^2$/g.

7. The process of claim 6 wherein said temperature is in the range from about 500° C. to about 600° C.

8. The process of claim 7 wherein the molar proportions of ethyl chloride to oxygen are in the range from about 1:0.25 to about 1:2.

9. The process of claim 8 wherein said catalyst also contains from about 0.1 to about 1% by weight of a platinum-group metal.

10. The process of claim 9 wherein said platinum-group metal is platinum.

11. The process of claim 9 wherein said catalyst also contains from about 0.5 to about 2.0% by weight of an alkali metal chloride.

* * * * *